United States Patent [19]

Hamprecht

[11] Patent Number: 4,808,723

[45] Date of Patent: Feb. 28, 1989

[54] PROCESS FOR THE PREPARATION OF BENZOTHIAZOLES

[75] Inventor: Rainer Hamprecht, Odenthal, Fed. Rep. of Germany

[73] Assignee: Bayer Aktiengesellschaft, Leverkusen, Fed. Rep. of Germany

[21] Appl. No.: 567,480

[22] Filed: Jan. 3, 1984

[30] Foreign Application Priority Data

Jan. 21, 1983 [DE] Fed. Rep. of Germany ....... 3301869
Oct. 18, 1983 [DE] Fed. Rep. of Germany ....... 3337859

[51] Int. Cl.⁴ ........................................... C07D 277/82
[52] U.S. Cl. ................................................... 548/164
[58] Field of Search ............... 548/152, 161, 178, 179, 548/180, 164

[56] References Cited

U.S. PATENT DOCUMENTS 2,575,614  11/1951  Cassaday et al. ................... 548/164

FOREIGN PATENT DOCUMENTS 0069445  1/1983  European Pat. Off.
670968   1/1939  Fed. Rep. of Germany ........ 12 P/4
410088   4/1934  United Kingdom.
502109   3/1939  United Kingdom.

OTHER PUBLICATIONS

Chemical Abstracts 56, 7293, (1962).
"Gmelin Handbuch der Anorganischen Chemie", L. Gmelin, Berlin-Heidelberg-New York, 1978, pp. 92–93.
"Un nuovo metodo di preparazione di alcuni solfuri aromatici", Giua M. e Rugger A., Gazz. chim. ital., 53, I 290, (1923), pp. 341–344.
Chemical Abstracts, A. Guia and A. Ruggeri, "A New Method of Preparation of some Aromatic Sulfides", II Gazz. chim ital., 53, p. 235.
"Chloronitrobenzenes and Thiocarbamides", J. Taylor and A. E. Dixon, Chem. Dept., University College, Cork, (1923), pp. 243–250.

Robert C. Elderfield, "Heterocyclic Compounds", vol. 5, p. 513.
March, "Advanced Organic Chemistry", 2nd Ed., p. 594.

*Primary Examiner*—Robert Gerstl
*Attorney, Agent, or Firm*—Sprung Horn Kramer & Woods

[57] ABSTRACT

Benzothiazoles of the formula

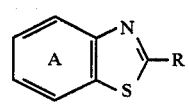
(I)

in which

R represents H, $NH_2$ or $R_1$, $R_1$ denoting alkyl or aryl, and it being possible for the ring A to have other substituents, are obtained in a simple manner by reacting the readily accessible compounds of the formula

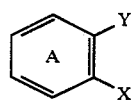
(II)

in which

X denotes a leaving group and
Y denotes $NO_2$ or $NH_2$, with specified amounts of a compound of the formula

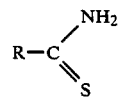
(III)

The compounds I are intermediates for dyestuffs and plant-protection agents.

4 Claims, No Drawings

PROCESS FOR THE PREPARATION OF BENZOTHIAZOLES

The invention relates to a process for the preparation of benzothiazole derivatives of the formula

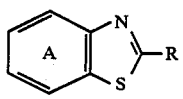

(I)

in which R represents H, $NH_2$ or $R_1$, $R_1$ denoting alkyl or aryl, and it being possible for the ring A to have other substituents, which is characterised in that appropriate aminobenzenes or nitrobenzenes which have a suitable leaving group in the ortho position are reacted with an appropriate thioamide or system which forms a thioamide, the reaction of o-aminothiophenol with ammonium thiocyanate according to European Pat. A No. 0,069,445 (Example 16) being excluded.

A preferred variant of the process is characterised in that a compound of the formula

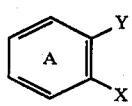

(II)

in which
X denotes halogen, $SO_3H$, $OSO_2R_1$, a radical of the formula (III)

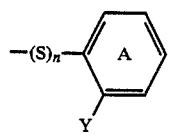

(III)

(n=1 or 2), but also SCN when Y denotes $NO_2$, and
Y denotes $NO_2$ or $NH_2$, is reacted with a compound which, in one of its possible tautomeric forms, corresponds to the formula

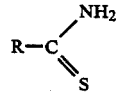

(IV)

or systems forming these compounds, it also being possible, in the case of reaction with preformed compounds of the formula IV, for the radical X also to denote SH.

Suitable alkyl radicals $R_1$ are straight-chain or branched, saturated or unsaturated alkyl radicals which can optionally be substituted by substituents which do not participate in the reaction (for example by CN or $C_1$–$C_4$-alkoxy) and preferably have 1–6C atoms (obviously at least 2C atoms in unsaturated radicals). The methyl radical is particularly preferred.

Suitable aryl radicals, which are mentioned in arbitrary sequence, are aromatic carbocyclic or heterocyclic radicals which likewise can be substituted by "inert" substituents, such as, for example, $C_1$–$C_4$-alkyl, $C_1$–$C_4$-alkoxy or halogen which is not activated.

Examples of suitable substituents in ring A are halogen, $R_1$, $-OR_1$, $-CN$, $-COR_1$, $-CO_2R_1$, $CON(R_1)_2$, $SO_3H$, $SO_2R_1$, $SO_2NH_2$, $SO_2N(R_1)_2$, $NO_2$, $CF_3$ or $-N=N-$aryl, "alkyl" and "aryl" also having the above-mentioned preferred meanings, and strongly electron-withdrawing substituents, which preferably appear in the 5-/7-position, being preferred. Moreover, it is possible for ring A to be fused with other rings, preferably of an aromatic nature.

"Halogen" is understood to include, preferably, chlorine or bromine.

Preferred compounds of the formula II are those of the formula

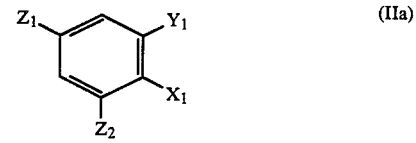

(IIa)

in which $Z_1$ and $Z_2$ denote hydrogen, Cl, Br, $NO_2$, $CF_3$, CN, $-CO-$alkyl, $-SO_2-$alkyl, $-SO_2-$phenyl, $-CO_2-$alkyl, $-CON(alkyl)_2$ or $-SO_2N(alkyl)_2$, $Z_1$ and $Z_2$ not both representing hydrogen, the alkyl radicals having 1–6 C atoms and it being possible for the phenyl radical to be substituted by Cl, Br, $NO_2$ or $C_1$–$C_4$-alkoxy, $X_1$ denotes chlorine, bromine, SH, SCN or a radical of the formula (IIIa)

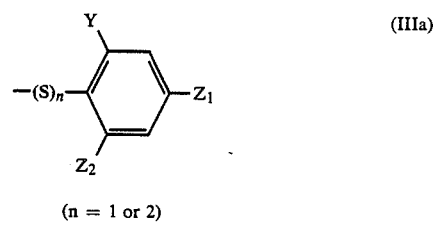

(IIIa)

(n = 1 or 2)

Y denotes $NO_2$ or $NH_2$, and $Y_1$ denotes $NO_2$ and, when $X_1 = SH$ or a radical of the formula (IIIa) with n=2, also denotes $NH_2$.

The sulphur-containing radicals X and the electron-withdrawing radicals $Z_1$ and/or $Z_2$ are particularly preferred.

Compounds of the formula (IIa) in which
$Z_1$ denotes $CF_3$, $SO_2CH_3$, $SO_2CH_2Cl$,
$SO_2C_2H_5$, $-SO_2C_6H_5$ and, in particular,
$NO_2$,
$Z_2$ denotes $CF_3$, $NO_2$ or, in particular, H,
$X_1$ denotes Cl, and
$Y_1$ denotes $NO_2$ are very particularly preferred.

Preferred compounds of the formula (IV) are those in which R represents $NH_2$, alkyl or aryl, the mentioned hydrocarbon radicals having the abovementioned general and specific meanings. Accordingly, suitable compounds of the formula (IV) are thioamides and, in particular, thiourea. These compounds, of which, moreover, the urea can also be in the form of its dioxide, are preferably employed as such (that is to say preformed) or are prepared "in situ" from appropriate systems which form the thioamide in the reaction mixture. Examples of "thioamide-formers" of this type are thiocyanates of the formula $NH_4^{\oplus}SCN^{\ominus}$ and $R_1-NH_3^{\oplus}SCN^{\ominus}$, $R_1$ representing $C_1$–$C_6$-alkyl or optionally substituted phenyl, and mixtures of nitriles of the formula $R_1-CN$ or $NH_2CN$ with $H_2S$ or compounds which liberate $H_2S$, it being the case that the hydrogen sulphide should preferably be present in excess.

While it is possible for the compounds of the formula (IV) to be in amounts equimolar with compounds of the formula II in which Y denotes NH$_2$, they must be employed in excess with respect to the compounds (II) with Y=NO$_2$. In general, a small excess of 5 to 10% of an equivalent is sufficient. However, preferably 2 to 10, and particularly preferably 3 to 6, equivalents of (IV) are used relative to (II).

In principle, the reaction of (II) with (IV) can be carried out without any diluent, advantageously in a relatively large excess of molten (IV). However, in most cases, it is advisable to undertake the reaction in the presence of a solvent which is inert under the reaction conditions, since the reaction is more or less strongly exothermic, and the resulting heat can thus be better conducted away.

Particularly suitale solvents are those of an organic nature, such as higher boiling alcohols (in particular propanol, butanols and pentanols), glycol ethers (for example methyl, ethyl and butyl glycol and diethylene glycol dimethyl ether), cyclic amides (for example N-methylpyrrolidone and caprolactam), ketones, such as, for example, diethyl ketone, and, in particular, tetrahydrothiophene 1,1-dioxide.

Water and aqueous two-phase systems (for example toluene/water) where appropriate in the presence of phase-transfer catalysts, are also suitable as solvents.

On the other hand, solvents having a carboxylic acid group are less suitable since they participate in the reaction under certain conditions.

In general, the reaction is carried out at temperatures from 60° to 250° C., preferably 70° to 200° C., and particularly preferably at 70° to 150° C.

In practice, compound (II) is introduced into a suspension or solution of compound (IV) or of the components from which compound (IV) is produced. The rate of introduction is such that the temperature is kept below a preset value. Where necessary, the reaction vessel may be cooled to control the temperature.

Addition of bases (for example tert.-amines or N-heterocycles) is frequently advantageous.

The end of the reaction or the completion of conversion is best found by thin-layer chromatography.

The products of the process, most of which are known, are valuable starting materials for a variety of industrial products. Their suitability for the preparation of azo dyestuffs (German Patent Specification No. 639,727), sensitisers (German Patent Specification No. 710,748), metal complex dyestuffs (German Offenlegungsschrift No. 2,848,622), herbicides (U.S. Pat. Specification No. 2,756,135) and polymethines having a wide spectrum of applications (compare Houben-Weyl, "Methoden der Organischen Chemie" (Methods of Organic Chemistry), 4th edition, Volume V/1a, pages 231 et seq.) should be picked out.

The new process is distinguished from the known Hugershoff synthesis (R. C. Elderfield, "Heterocyclic Compounds", Vol. 5, 581 et seq., John Wiley & Sons, New York 1957 and German Offenlegungsschrift No. 2,631,163) by the procedure being particularly straightforward, since 2-aminobenzothiazoles are formed in a one-step reaction from starting materials which are readily accessible industrially, such as, for example, o-chloronitrobenzene derivatives, while it is necessary in the method of Hugershoff for the appropriate phenylthioureas first to be prepared from aniline derivatives and then cyclised, using oxidising agents in a second step of the process, to give 2-aminobenzothiazoles.

Another disadvantage of the Hugershoff synthesis is regarded as being the production, in the case of meta-substituted anilines, of products which are not homogeneous but are mixtures of 5- and 7-substituted 2-aminobenzothiazoles (compare German Offenlegungsschrift No. 2,602,173=U.S. Pat. Specification No. 4,052,379). Moreover, the Hugershoff process is limited, in particular, by phenylthioureas having strongly electronegative substituents being not easily accessible and, in some cases, it being necessary to take indirect routes via the appropriate acylphenylthioureas (German Offenlegungsschrift No. 2,602,173).

Similar disadvantages apply to the oxidative reaction of anilines with thiocyanates (compare Die Pharmazie, 32, 195, (1977)).

EXAMPLE 1

Preparation of 2-amino-5-nitrobenzothiazole

A suspension of 10.13 g of 2,4-dinitrochlorobenzene and 15.2 g of thiourea in 50 ml of sulpholane (tetrahydrothiophene 1,1-dioxide) is stirred at 110° to 120° C. for 12 hours. After cooling, the mixture is thoroughly stirred with 800 ml of water, and the solid is filtered off with suction and washed with water. After drying, 11.2 g of a yellow powder which, according to HPLC analysis (high pressure liquid chromatography), contains 69.5% of 2-amino-5-nitrobenzothiazole (corresponding to 80% of theory) are obtained. Recrystallisation from dimethylformamide raises the melting point to 307° C. (decomposition) (Zhur. Obschei Khim. 30, 1363-6 (1960) reports melting point 308°-309° C., decomposition).

EXAMPLE 2

Preparation of 2-amino-5-nitrobenzothiazole

A solution of 10.13 g of 2,4-dinitrochlorobenzene and 15.2 g of thiourea in 50 ml of pyridine is boiled, with stirring, under a reflux condenser for 3 hours. After cooling, the mixture is thoroughly stirred with 500 ml of water, and the solid is filtered off with suction, washed with water and dried. 11.6 g of 2-amino-5-nitrobenzothiazole having a purity of 66% by HPLC analysis, corresponding to a yield of 78.5% of theory, are obtained.

EXAMPLE 3

Preparation of 2-amino-5-nitrobenzothiazole

A suspension of 5.06 g of 2,4-dinitrochlorobenzene and 7.6 g of ammonium thiocyanate in 25 ml of sulpholane is heated, with stirring, to 150° C. and maintained at this temperature for 1.5 hours. The product is discharged into 300 ml of water, and the solid is filtered off with suction and washed with water. After drying, 6.57 g of crude 2-amino-5-nitrobenzothiazole are obtained. The identity was confirmed by TLC comparison (TLC=thin-layer chromatography) with authentic material.

EXAMPLE 4

Preparation of 2-amino-5-nitrobenzothiazole 11.71 g of 2,4-dinitrophenyl thiocyanate are added, over the course of 15 minutes, to a solution of 7.6 g of thiourea in 50 ml of dimethylformamide at 150° C. The mixture is stirred at 150° C. for a further 2 hours, and the product is discharged into 500 ml of water, and the solid is filtered off with suction and washed with water.

11 g of crude 2-amino-5-nitrobenzothiazole are obtained, its identity being confirmed by TLC comparison with authentic material.

EXAMPLE 5

Preparation of 2-amino-5-nitrobenzothiazole

A solution of 10 g of 2,4-dinitrothiophenol and 7.6 g of thiourea in 50 ml of dimethylformamide is heated at 120° C. for 3 hours. The mixture is diluted with 300 ml of water, and the solid is filtered off with suction and washed with water. 7.3 g of crude 2-amino-5-nitrobenzothiazole, the identity of which was confirmed by TLC comparison with authentic material, are obtained.

EXAMPLE 6

Preparation of 2-amino-5-nitrobenzothiazole

A solution of 5.97 g of 2,4,2',4'-tetranitrodiphenyl disulphide and 4.56 g of thiourea in 40 ml of dimethylformamide is stirred at 120° C. for 3 hours. The mixture is discharged into 300 ml of water, and the solid is filtered off with suction and washed with water. 4.5 g of crude 2-amino-5-nitrobenzothiazole of melting point 290°–300° C. (decomposition) are obtained.

EXAMPLE 7

Preparation of 2-amino-5-nitrobenzothiazole 9.15 g of 2,4,2',4'-tetranitrodiphenyl sulphide are added in 15 minutes to a solution of 7.6 g of thiourea in 50 ml of dimethylformamide at 120° C., and stirring is continued at this temperature for 2 hours. The mixture is diluted with 300 ml of water, and the solid is filtered off with suction and washed with water. 7.6 g of crude 2-amino-5-nitrobenzothiazole of melting point 290°–300° C. (decomposition) are obtained.

EXAMPLE 8

Preparation of 2-amino-5-nitrobenzothiazole

A solution of 8.63 g of 2-chloro-5-nitroaniline and 9.9 g of sodium sulphide trihydrate in 80 ml of butyl glycol was stirred at 80° C. for 30 minutes. After adding 4.16 ml of concentrated sulphuric acid, 7.6 g of thiourea were added to the 2-amino-4-nitrothiophenol, and the mixture was stirred at 120° C. for 3 hours. The reaction mixture was discharged into 400 ml of water and 50 ml of methanol, and the solid was filtered off with suction and washed with water. 5.4 g of crude 2-amino-5-nitrobenzothiazole, the identity of which was confirmed by TLC comparison with authentic material, were obtained.

EXAMPLE 9

Preparation of 2-amino-5-nitrobenzothiazole

A solution of 6.76 g of 2,2'-diamino-4,4'-dinitrodiphenyl disulphide (Hodgson and Dodgson, J. Chem. Soc. 1948, 870) and 6.08 g of thiourea in 40 ml of sulpholane was stirred at 130° C. for 2 hours. The mixture was diluted with 300 ml of water, and the solid was filtered off with suction and washed with water. 7.2 g of crude 2-amino-5-nitrobenzothiazole, the identity of which was confirmed by TLC comparison with authentic material, were obtained.

EXAMPLE 10

Preparation of 2-methyl-5-nitrobenzothiazole

A suspension of 10.13 g of 2,4-dinitrochlorobenzene and 15 g of thioacetamide in 50 ml of sulpholane was heated to 100° C. and stirred at this temperature for 1 hour. After cooling, the mixture was clarified. 200 ml of water were added to the filtrate. The solid was filtered off with suction, washed with water and dried.

Yield: 6.02 g of material which is homogeneous by thin-layer chromatography. Recrystallisation from ethanol raises the melting point to 133° C. (J. Chem. Soc. Perkin Trans. 1, 1973, 356–359 reports melting point 135°–137° C.). $m_e^+$: 194.

EXAMPLE 11

Preparation of 2-amino-5-nitro-7-trifluoromethylbenzothiazole 13.5 g of 2-chloro-3,5-dinitrobenzotrifluoride is slowly introduced, with stirring, into a solution of 15.2 g of thiourea in 50 ml of sulpholane at 100° C. The mixture is stirred at 100° C. for a further 2.5 hours, cooled and the solid is filtered off with suction and the dry residue is thoroughly stirred with 50 ml of carbon disulphide. The solid is filtered off with suction and 7.5 g of material, which is homogeneous by chromatography and has a melting point of 303°–307° C. (decomposition), are obtained. After recrystallisation from pyridine/water (3/1), the melting point rises to 315°–316° C. (decomposition). $m_e^+$: 263

EXAMPLE 12

Preparation of 2-amino-5-trifluoromethyl-7-nitrobenzothiazole 67.5 g of 4-chloro-3,5-dinitrobenzotrifluoride are slowly introduced, with stirring, into a solution of 76 g of thiourea in 250 ml of sulpholane at 100° C. The mixture is stirred at 100° C. for a further one hour. After cooling, the precipitate is filtered off with suction and dried. 35.7 g of crude 2-amino-5-trifluoromethyl-7-nitrobenzothiazole of melting point 254°–256° C. (decomposition) are obtained. Recrystallisation from pyridine/water (3/1) raises the melting point to 262°–263° C. $m_e^+$: 263.

A further 28.7 g can be precipitated from the filtrate of the crude product by addition of 500 ml of water.

EXAMPLE 13

Preparation of 2-amino-5-ethanesulphonylbenzothiazole

A suspension of 12.8 g of ethyl 4-chloro-3-nitrophenyl sulphone and 15.2 g of thiourea in 50 ml of sulpholane is heated to 120° C. and this temperature is maintained for 1.5 hours. The mixture is discharged into 600 ml of water, and the solid is filtered off with suction and washed with water. 10.6 g of colourless 2-amino-5-ethanesulphonylbenzothiazole are obtained.

$\lambda_{max}$ = 234 nm (CH$_3$CN). $m_e^+$: 242.

EXAMPLE 14

Preparation of 2-amino-5-benzenesulphonylbenzothiazole 14,9 g 4-Chloro-3-nitrodiphenyl sulphone is introduced into a solution of 15.2 g of thiourea in 50 ml of sulpholane at 150° C., and this temperature is maintained for 1 hour. The mixture is discharged into 500 ml of water, and the solid is filtered off with suction and washed with water. The dry product is vigorously stirred with 50 ml of carbon disulphide. The solid is filtered off with suction and 15.5 g of crude 2-amino-5-benzenesulphonylbenzothiazole are obtained, $m_e^+$: 290,

EXAMPLE 15

Preparation of 2-amino-5-chloromethanesulphonylbenzothiazole 13.83 g of chloromethyl 4-chloro-3-nitrophenyl sulphone are introduced into a solution of 15.2 g of thiourea in 50 ml of sulpholane at 150° C., and this temperature is maintained for 1 hour. Working up is as in Example 14 and 10 g of 2-amino-5-chloromethanesulphonylbenzothiazole are obtained. $m_e^+$: 262, $\lambda_{max}=238$ nm ($CH_3CN$).

EXAMPLE 16

Preparation of 2-aminobenzothiazole

A suspension of 9.5 g of 2,2'-dinitrophenyl disulphide and 15.2 g of thiourea in 50 ml of sulpholane was stirred at 100° C. for 4 hours and at 150° C. for a further 4 hours. The mixture was clarified and the filtrate was discharged into 250 ml of water. The precipitate, which was initially oily, was recrystallised from ethanol. 0.54 g of 2-aminobenzothiazole, the identity of which was confirmed by TLC comparison with authentic material, was obtained.

I claim:

1. A process for the preparation of a benzothiazole of the formula

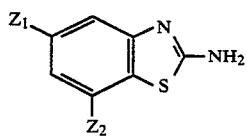

in which $Z_1$ and $Z_2$ each independently is hydrogen, Cl, Br, $NO_2$, $CF_3$, CN, —CO-alkyl, —$SO_2$-alkyl, —$SO_2$-phenyl, —$CO_2$-alkyl, —CON(alkyl)$_2$ or —$SO_2$—N(alkyl)$_2$, the alkyl radicals having 1-6C atoms, but $Z_1$ and $Z_2$ are not both simultaneously hydrogen, comprising reacting (a) a compound of the formula

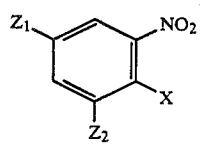

in which
X is chlorine, bromine, SH, SCN or a radical of the formula

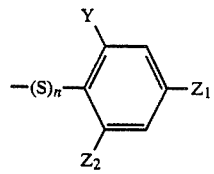

Y is $NO_2$ or $NH_2$, and
n is 1 or 2,
with (b)

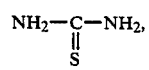

$NH_4^+SCN^-$ and a mixture of $H_2NCN$ or $H_2S$,
(b) being employed in at least a 5% excess relative to 1 equivalent of (a).

2. A process according to claim 1, wherein 3 to 6 equivalents of (b) are reacted with 1 equivalent of (a).

3. A process according to claim 1 in which
$Z_1$ is $CF_3$, $SO_2CH_3$, $SO_2CH_2Cl$, $SO_2C_2H_5$, $SO_2C_6H_5$ or $NO_2$,
$Z_2$ is H, $CF_3$ or $NO_2$, and
X is Cl.

4. A process according to claim 1, wherein (b) is thiourea.

* * * * *